United States Patent
Muir et al.

(10) Patent No.: US 7,087,557 B2
(45) Date of Patent: Aug. 8, 2006

(54) METAL-CONTAINING NEUTRAL AND OVERBASED SALICYLATES BASED ON STYRENATED SALICYLIC ACID

(75) Inventors: Ronald J. Muir, West Hill (CA); William D. Olson, Toronto (CA)

(73) Assignee: Crompton Co./Cie, Ontario (CA)

( * ) Notice: Subject to any disclaimer, the term of this patent is extended or adjusted under 35 U.S.C. 154(b) by 436 days.

(21) Appl. No.: 10/626,747

(22) Filed: Jul. 22, 2003

(65) Prior Publication Data

US 2004/0138076 A1 Jul. 15, 2004

Related U.S. Application Data

(60) Provisional application No. 60/397,676, filed on Jul. 23, 2002.

(51) Int. Cl.
C10M 159/22 (2006.01)
(52) U.S. Cl. ...................................... 508/460; 508/457
(58) Field of Classification Search ................. 508/460
See application file for complete search history.

(56) References Cited

U.S. PATENT DOCUMENTS

| | | | |
|---|---|---|---|
| 3,438,899 A | 4/1969 | Benoit | 252/51.5 |
| 4,617,135 A | 10/1986 | Muir | 252/33.2 |
| 4,647,387 A | 3/1987 | Muir | 252/25 |
| 4,748,259 A | 5/1988 | Nachbur | 556/132 |
| 4,810,398 A | 3/1989 | Van Kruchten et al. | 252/40 |
| 4,832,857 A | 5/1989 | Hunt et al. | 252/33 |
| 4,869,837 A | 9/1989 | van Wijngaarden et al. | 252/39 |
| 4,995,993 A | 2/1991 | Papke et al. | 252/25 |
| 5,049,294 A | 9/1991 | Van Zon et al. | 252/51.5 |
| 5,075,416 A | 12/1991 | Staglich et al. | 528/179 |
| 5,147,570 A | 9/1992 | Van Zon et al. | 252/51.5 |
| 5,225,588 A | 7/1993 | Senaratne et al. | 560/71 |
| 5,415,792 A | 5/1995 | Campbell | 252/18 |
| 5,647,896 A | 7/1997 | Nishimura et al. | 106/31.18 |
| 5,734,078 A | 3/1998 | Feilden et al. | 562/477 |
| 5,744,430 A | 4/1998 | Inoue et al. | 508/295 |
| 6,107,259 A | 8/2000 | Muir et al. | 508/393 |
| 6,140,281 A | 10/2000 | Blahey et al. | 508/398 |
| 6,140,282 A | 10/2000 | Cartwright et al. | 508/398 |
| 6,191,081 B1 | 2/2001 | Cartwright et al. | 508/460 |
| 6,197,075 B1 | 3/2001 | Muir et al. | 44/373 |
| 6,239,083 B1 | 5/2001 | Muir | 508/393 |
| 6,255,258 B1 | 7/2001 | Clark et al. | 508/232 |
| 6,284,717 B1 | 9/2001 | Crane et al. | 508/258 |
| 6,303,550 B1 | 10/2001 | Wedlock et al. | 508/591 |
| 6,372,696 B1 | 4/2002 | Tipton | 508/110 |

FOREIGN PATENT DOCUMENTS

| | | |
|---|---|---|
| EP | 1072623 A2 | 1/2001 |
| EP | 1072623 A3 | 1/2001 |
| GB | 1570909 | 7/1980 |
| WO | WO 01/56968 A1 | 8/2001 |

OTHER PUBLICATIONS

Lewis, Sr., Richard J.; Hawley's Condensed Chemical Dictionary 12th Ed., John Wiley & Sons, New York, 1993 (pp. 34 and 98).*

* cited by examiner

Primary Examiner—Matthew A. Thexton
(74) Attorney, Agent, or Firm—Michael P. Dilworth

(57) ABSTRACT

A salicylate is disclosed, which has detergent and antioxidant properties, for use as a metal based detergent additive. An alkyl salicylic acid is derived from the alkylation of salicylic acid with styrene. The neutralization and subsequent overbasing of neutral salt results in an alkaline detergent, such as calcium or magnesium salicylate. The resulting detergent is a salicylic acid having multi-styrenated chains, which provide oil solubility. A method for making such a detergent is also disclosed.

10 Claims, No Drawings

METAL-CONTAINING NEUTRAL AND OVERBASED SALICYLATES BASED ON STYRENATED SALICYLIC ACID

I claim the benefit under Title 35, United States Code, § 120 to U.S. Provisional Application No. 60/397,676, filed Jul. 23, 2002, entitled METAL-CONTAINING NEUTRAL AND OVERBASED SALICYLATES BASED ON STYRENATED SALICYLIC ACID.

BACKGROUND OF THE INVENTION

1. Field of the Invention

The present invention relates to engine oils. More particularly, the present invention relates to overbased detergents for use in engine oils, especially metal-containing neutral and overbased salicylates based on styrenated salicylic acid that provide excellent detergency and clarity in a lubricating oil, and to a method for making such detergents.

2. Description of Related Art

Among the materials that impart detergency to lubricating oils to keep internal engine parts clean and reduce sludge formation in the oil are overbased detergents, particularly calcium sulfonates. These sulfonates are known to be useful as additives for lubricating oils, particularly as a crankcase engine oil for internal combustion engines.

It is known that by use of such overbased detergents equivalent detergency characteristics can be obtained with a lower concentration of additive in a lubricating oil—the higher the alkaline reserve of an additive, the larger the quantity of acidic combustion products accumulated in the oil to which the additive is added that can be neutralized by the additive. The measurement of alkaline reserve is reported as total base number (TBN) which is the number of milligrams of potassium hydroxide equivalent to the amount of acid required to neutralize the alkaline constituents present in one gram of sample. An additive having a total base number higher than can be obtained from calcium petroleum sulfonate alone is commonly said to be "overbased" or, alternatively, is said to be "superbasic".

Overbased calcium sulfonates are generally produced by carbonating a mixture of hydrocarbons, sulfonic acid, calcium oxide, or calcium hydroxide and promoters, such as methanol and water. In carbonation, the calcium oxide or hydroxide reacts with the gaseous carbon dioxide to form calcium carbonate. The sulfonic acid is neutralized with an excess of CaO or $Ca(OH)_2$ to form the sulfonate. Known processes for overbasing calcium sulfonates produce high alkaline reserves of TBN of 300 to 400 mg KOH/gm or higher, which enables the formulator to use lower amounts of additive while maintaining equivalent detergency to protect the engine adequately under conditions of high acid formation in the combustion process.

The calcium carbonate component of the overbased calcium sulfonate forms the core of a calcium sulfonate micellar structure. The calcium carbonate is either in the amorphous form or one or more of its crystalline forms, such as calcite.

The lubricating oil art, particularly as directed to automotive crankcase and other engine oils, mandates a clear or substantially haze free product for requisite consumer aesthetics and acceptance. This need previously precluded the use of detergents with haze producing crystalline calcium carbonate.

It was recognized in U.S. Pat. No. 4,995,993 that large micellar crystalline calcium carbonate structures caused haze, and overbased sulfonate products containing crystalline calcium carbonates were always undesirable and therefore crystallization was to be avoided at all costs.

In "Colloidal Anti-wear Additives 2. Tribological Behavior of Colloidal Additives in Mild Wear Regime," J. L. Mansot et al., Colloids and Surfaces A: Physico Chemical and Engineering Aspects, 75 (1993), pp. 25–31, it is indicated that for certain forms of an overbased sulfonate containing an amorphous calcium carbonate core, when in a 2% by weight dispersion in dodecane, and subjected to metallic friction surfaces, the calcium carbonate forms a polycrystalline film adherent to the metallic friction surfaces, which resultantly provides anti-wear protection. Mansot et al. thereby taught providing an overbased calcium sulfonate with an amorphous micellar structure that would then, under a mild wear regime, undergo transformation to microcrystalline agglomerates through an amorphous intergranular phase.

WO 0004113 discloses a process for producing soluble overbased calcite-containing detergents that are suitable for use in engine oil formulations.

U.S. Pat. No. 4,617,135 discloses a process for the preparation of overbased oil soluble magnesium sulfonates comprising contacting an acidic gas at a temperature between about 50° F. up to the reflux temperature of the mixture, with a mixture consisting essentially of a sulfonic acid or salt thereof, a volatile aliphatic or aromatic or chlorinated hydrocarbon solvent, a non-volatile diluent oil, a light magnesium oxide, water, methanol and combination of promoters, wherein the first promoter is one selected from an oil soluble naphthenic acid and an oil soluble carboxylic acid or salt thereof; and a second promoter being one selected from:

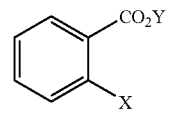

wherein X is one of H, OH, $NH_2$, $CO_2H$, $OCOCH_3$ and SH, and Y is one of H, $CH_3$ and $CH_2CH_3$, wherein the second promoter is less oil soluble than the first promoter; and (b) a water soluble $C_1$–$C_6$ carboxylic acid. The volatile components are stripped from the reaction mixture after absorption of the acidic gas is completed, to give an overbased magnesium sulfonate. Relatively small amounts of about 1.0 to 1.5% of the combined promoters produce overbased magnesium sulfonates of exceptionally high alkalinity value up to 500 or more, with minimum sediment.

U.S. Pat. No. 4,647,387 discloses an engine or lubricating oil containing 0.03 to 0.3% by weight of a succinic anhydride promoter reaction product for an overbased magnesium sulfonate, based on the presence of 0.5% by weight of Mg metal in the oil, and wherein the weight of the reaction product is commensurately proportional to the weight of Mg metal in the oil, and which oil is free of post sulfonate formation water-tolerance additives, nevertheless passes the rigorous Cummins water tolerance test. Copromoters such as a naphthenic acid and/or a salicylic acid may be employed.

U.S. Pat. No. 4,748,259 discloses mixtures of a metal salt of formula

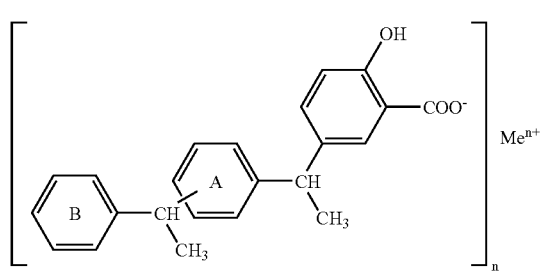

and a metal salt of formula

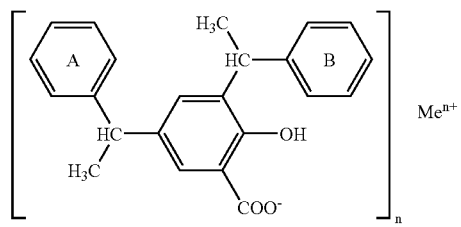

in which formulae, Me is a metal ion of valency n, n is 2, 3 or 4, and each of the rings A and B independently of the other is unsubstituted or substituted by halogen, lower alkyl, lower alkoxy or an α-methylbenzyl radical, are prepared by reacting 2 moles of salicylic acid with at least 2 moles of a styrene compound of formula

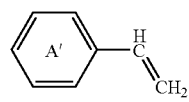

and at least 2 moles of a styrene compound of formula

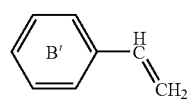

in which formulae, the benzene rings A' and B' are unsubstituted or substituted by halogen, lower alkyl or lower alkoxy, in the presence of an aromatic sulfonic acid, and, in a further step, reacting 2n moles of the resultant mixture of the salicylic acid compound of formula

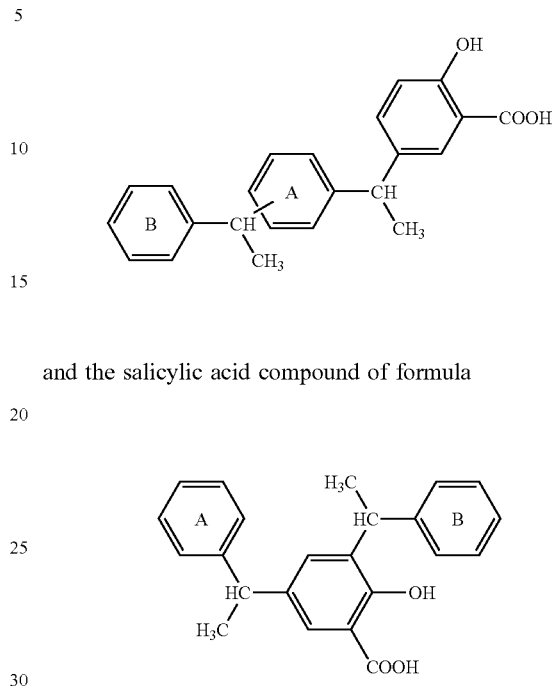

in which formulae, A and B are as defined above, with 2 moles of the salt of an n-valent metal of an inorganic acid or of a lower aliphatic carboxylic acid, where n has the given meaning. The mixtures of metal salts are used as color formers in pressure- and heat-sensitive recording materials.

U.S. Pat. No. 4,810,398 discloses a basic alkaline earth metal salt of a blend of organic carboxylic acids that is prepared by (a) preparing a mixture of one equivalent of the blend of organic carboxylic acids and more than one equivalent of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises a $C_{8-30}$ alkyl salicylic acid and one or more alkanecarboxylic acids in which the alkyl moiety is branched and has from 4 to 40 carbon atoms. Such a salt has dispersant properties and is said to be suitable for use in lubricating oil and fuel compositions.

U.S. Pat. No. 4,832,857 discloses a process for incorporating molybdenum into overbased alkaline earth metal and alkali metal sulfonates, phenates and salicylates. The incorporation is a post addition of molybdenum into a previously prepared overbased composition. The resulting composition containing molybdenum is said to have a reproducible TBN and to be gel-free, haze-free, precipitate-free, and commercially acceptable for use in lubricating oil compositions.

U.S. Pat. No. 4,869,837 discloses a process for the preparation of a basic alkaline earth metal salt of a blend of organic carboxylic acids, which comprises (a) preparing a mixture of one equivalent of the blend of organic carboxylic acids and more than one equivalent of an alkaline earth metal hydroxide and/or oxide in a hydrocarbon solvent; (b)

introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises an oil-soluble alkyl salicylic acid and one or more hydrocarbon substituted succinic acids or anhydrides, in which the hydrocarbon radical has a number average molecular weight from 120 to 5000.

U.S. Pat. No. 5,075,416 discloses a process for the preparation of an aromatic hydrocarbon resin modified with aromatic carboxylic acids comprising suspending methane sulfonic acid and at least one aromatic carboxylic acid in an aliphatic solvent and slowly proportioning at least one unsaturated aromatic hydrocarbon into the suspension under polymerization conditions and their salts.

U.S. Pat. No. 5,225,588 discloses alkylating hydroxybenzoates, such as methylsalicylate, by reacting a hydroxybenzoate with a polyalphaolefin in the presence of a catalytic amount of $SnCl_4$.

U.S. Pat. No. 5,415,792 discloses overbased alkyl alkyl salicylate that are said to be useful additives for lubricating oil compositions that impart detergency and dispersancy to the lubricating oil composition and provide for alkalinity reserve.

U.S. Pat. No. 5,647,896 discloses a color-developing agent comprising a multivalent metal salt of a salicylic acid derivative and a sulfonated phenol and/or a metal salt thereof and having excellent initial and ultimate color-developing capacities and improved waterproofness; and a color-developing sheet making use of the color-developing agent.

U.S. Pat. No. 5,734,078 discloses a process for the production of an alkyl salicylic acid in which the alkyl substituent has at least 6 carbon atoms, comprising reacting salicylic acid with an olefin having at least 6 carbon atoms at elevated temperature in the presence of sulphuric acid as a catalyst. Lubricating oil additives comprising a metal salt of such alkylated salicylic acids and a process for making them are also disclosed.

U.S. Pat. No. 5,744,430 discloses a composition having therein a base oil with a specified kinematic viscosity and with a specified total amount of aromatics, comprising, in specified amounts based on the total weight of the composition: (b) an alkaline earth metal salicylate detergent; (c) a zinc dialkyldithiophosphate; (d) a succinimide ashless dispersant containing a polybutenyl group having a specified number-average molecular weight; (e) a phenol ashless antioxidant; (f) a molybdenum dithiocarbamate friction modifier; and (g) a viscosity index improver in such an amount that the kinematic viscosity of said composition ranges from 5.6 to 12.5 $mm^2/s$ at 100° C.

U.S. Pat. No. 6,197,075 discloses an overbased magnesium composition deposit control additive for residual fuel oils and turbine fuels that is an overbased magnesium sulfonate, carboxylate or phenate or mixtures thereof containing at least 14% and upwards to about 18% by weight of magnesium and containing a succinic anhydride and lower carboxylic acid co-promoter reaction product. The additive when added to fuel oils, such as residual fuel oils containing high asphaltenes, reduces, if not eliminates, magnesium/ asphaltene deposits or sediment and the consequential plugging of filters. The additive also reduces, if not eliminates, vanadium caused corrosion in the turbine. Also disclosed is a process for preparing the overbased composition or deposit control additive, wherein the overbasing reaction incorporates the combination of a lower carboxylic acid, preferably acetic acid and a succinic anhydride, preferably dodecenyl succinic anhydride, as the co-promoter.

U.S. Pat. No. 6,303,550 discloses a lubricating oil composition comprising a di-block copolymer of poly(monovinyl aromatic hydrocarbon) and hydrogenated poly(conjugated diene) as a dispersant additive. The di-block copolymer preferably comprises poly(monovinyl aromatic hydrocarbon) in the molecular weight range 8,000–30,000. The diblock copolymers are said to be useful as dispersant additives in lubricant oils, reduce heavy metal corrosion, reduce degradation of elastomeric seals and are less sensitive to the presence of over-based detergents.

There remains a need in the art for a lubricating oil detergent with inherent improved high temperature detergency which also necessarily has commercially acceptable levels of minimal haze, or are essentially haze free, and acceptable minimal levels of turbidity. In particular, there remains a need for an automotive oil having improved detergency and antioxidant properties for use as a crankcase engine oil.

The compositions of this invention also are suitable for use in either low or medium speed engines especially marine diesel engines. Typically such engines are 4 stroke trunk piston engines having an engine speed of 50–1000 RPM. The engine can also be a 2 stroke cross head engine having a speed 40–1000 RPM.

SUMMARY OF THE INVENTION

A novel salicylate detergent has been developed with outstanding detergency and anti-oxidant properties. While the current art utilizes a hydrocarbon backbone typically derived from an α-olefin having from 8 to 20 carbons, it has now been found that alkyl salicylic acid derived from the alkylation of salicylic acid with styrene makes suitable salicylic acid that can be used to make metal based detergent additives.

The neutralization and subsequent overbasing of neutral salt results in alkaline detergents, such as calcium or magnesium salicylates, that have detergency and anti-oxidant properties superior to existing salicylate detergents. Thus, the present invention is directed to the use of salicylic acid having multi-styrenated chains, which provide oil solubility, in the manufacture of oil soluble metal detergents.

More particularly, the present invention is directed to an engine oil comprising a lubricating oil, and an overbased alkaline earth salicylate detergent of the structure:

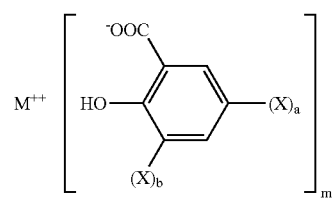

wherein:
X is

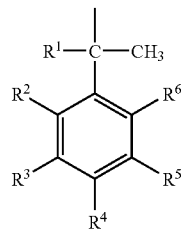

R¹ is selected from the group consisting of hydrogen, substituted or unsubstituted alkyl, and substituted or unsubstituted aryl;
$R^2$, $R^3$, $R^4$, $R^5$, and $R^6$ are independently selected from the group consisting of hydrogen, X, and innocuous functional groups;
a and b are independently selected integers $\geq 0$ and $a+b \geq 8$;
m is 2; and
M is an alkaline earth metal.

DESCRIPTION OF THE PREFERRED EMBODIMENTS

The alkaline earth metal salicylate detergents of the present invention suitably include a calcium salicylate detergent, a magnesium salicylate detergent, or a mixture thereof. In addition, these detergents can be neutral alkaline earth metal salicylates, overbased alkaline earth metal salicylate, or combinations thereof. The neutral alkaline earth metal salicylate as used herein is a salt in which the aromatic compound-substituted salicylic acid is neutralized with equivalent moles of an alkaline earth metal hydroxide. Such a neutral alkaline earth metal salicylate can be represented by the following general formula (I):

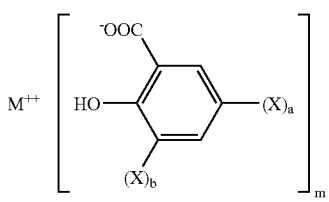

wherein:
X is

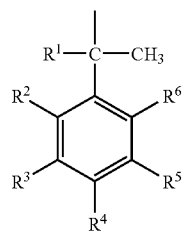

R¹ is selected from the group consisting of hydrogen, substituted or unsubstituted alkyl, and substituted or unsubstituted aryl;

$R^2$, $R^3$, $R^4$, $R^5$, and $R^6$ are independently selected from the group consisting of hydrogen, X, and innocuous functional groups;
a and b are independently selected integers $\geq 0$ and $a+b \geq 8$, preferably in the range of from 8 to 40;
m is 2; and
M is an alkaline earth metal, preferably calcium or magnesium.

Where R¹ is alkyl, it is preferred that it be lower alkyl, i.e., methyl, ethyl, propyl, butyl, or an isomer of propyl or butyl, e.g., tert-butyl. It is preferred that R¹ be hydrogen or methyl.

Where R¹ is substituted, it may be substituted with any innocuous moiety. As employed herein, the term "innocuous" is intended to mean a moiety that does not adversely affect the desired properties of the alkaline earth metal salicylate detergent, although they may, of course, provide beneficial effects.

Where R¹ is aryl, it is preferred that it be aryl of from 6 to 14 carbon atoms, e.g., phenyl, biphenyl, naphthyl, anthracyl, phenanthryl, and the like. More preferably, where R¹ is aryl, it is substituted or unsubstituted phenyl. Again, those skilled in the art will understand that any substituents will be innocuous, as defined above.

Those skilled in the art will also recognize that X in the above structural formula can be considered a styrenic-type moiety. Examples of such styrenic-type moieties include, but are not limited to, styrene; 2, 3,or 4-methylstyrene; 2 or 4-ethylstyrene; 3 or 4-isopropylstyrene; 4-n-butylstyrene; 4-t-butylstyrene, 4-cyclohexylstyrene; 4-octylstyrene; 2,4-dimethylstyrene; 2,5,dimethylstyrene; 3- or 4-methoxystyrene, 4-ethoxystyrene; α-methylstyrane; α-ethylstyrene; α-n-butylstyrene; α-isobutylstyrene; 4-phenylstyrene; 4-fluorostyrene; and the like. Styrene is preferred.

Overbased alkaline earth metal salicylates may be obtained by overbasing a neutral alkaline earth metal salicylate to produce an alkaline earth metal carbonate, such as calcium carbonate and magnesium carbonate, or an alkaline earth metal borate, such as magnesium borate.

The base number of the metal salicylate detergent is not particularly limited; however, the base number is normally in the range of from about 60 to about 350 mg KOH/g, preferably from about 150 to about 350 mg KOH/g.

It has been pointed out above that a+b in the formula is greater than 7, i.e., 8 or more, preferably 8 to 40, more preferably 8 to 20. Where a+b is at the lower end of this range, e.g., 8, it has been found that the solubility of the compound in oil will be less than will normally considered desirable. As more vinyl aromatic units are added to the chain attached to the salicylic acid moiety, i.e., as a+b increases, oil solubility will increase. If it is desired to use a compound wherein a+b is about 8, oil solubility can be improved by the addition of another overbased compound, e.g., overbased calcium sulfonate. For detergent additives of the present invention having sufficient vinyl aromatic groups present to render the compound oil soluble, the inclusion of the overbased calcium sulfonate or the like can be dispensed with.

In general, the process of preparing the overbased calcium salicylates of the present invention comprises reacting a solution of styrenated salicylic acids and, optionally, calcium sulfonate or sulfonic acid (for convenience, the following discussion will focus on calcium compounds, but those skilled in the art will readily comprehend that, by analogy, the process can be applied to magnesium compounds, as well as to calcium and magnesium mixtures) in oil with a slurry of calcium oxide or hydroxide and bubbling carbon dioxide through the reaction mixture, thereby incorporating an excess of calcium carbonate into the calcium salicylate and, if present, calcium sulfonate, which confers the desired reserve alkalinity to the product. In this process, it has been found advantageous to add a low molecular weight alcohol, such as methanol, and water to promote the formation of a micellar dispersion of calcium carbonate.

Calcium hydroxide when used commercially as the sole reserve alkalinity agent in the reaction mixture is used in substantial excess in order to achieve a high TBN product.

A dispersant is an optional component of the process and product for the calcite overbased detergent. A preferred dispersant is the reaction product of hydrocarbyl-substituted succinic acid or anhydride with amines containing at least one primary or secondary amino nitrogen, e.g., the polyalkylene polyamines fulfill this requirement as do the substituted polyalkylene polyamines, and for that matter, ammonia. The bis-succinimides are also useful as optional dispersants. The bis-succinimides are prepared by the reaction of hydrocarbyl-substituted succinic acid or anhydride with an amine containing at least two primary and/or secondary nitrogens. Such bis-succinimides are, for example, the polyisobutenyl bis-succinimides of ethylene diamine, diethylene traimine, or triethylene tetramine, or tetraethylene pentamine or N-methyldipropylene triamine, etc. (e.g., Benoit, U.S. Pat. No. 3,438,899). The various above-described dispersing agents can be used alone or in mixtures.

The overbased calcium salicylate product of the present invention has an amorphous micellar structure. The overbased calcium salicylate, or like overbased detergent, is a stable dispersion of amorphous calcium carbonate.

The overbased calcium salicylate detergent of the present invention may be added to engine or lubricating oils in detergent amounts of about 0.1 to 25% by weight or more, and are soluble in such oils at room temperature if a+b is high enough or if overbased calcium sulfonate is present, where a+b is low.

The present invention is applicable to a wide variety of lubricating oils. The lubricating oil can be composed of one or more natural oils, one or more synthetic oils, or mixtures thereof. Natural oils include animal oils and vegetable oils (e.g., castor, lard oil), liquid petroleum oils, and hydrorefined, solvent-treated or acid-treated mineral lubricating oils of the paraffinic, naphthenic and mixed paraffinic types. Oils of lubricating viscosity derived from coal or shale are also useful base oils.

Synthetic lubricating oils include hydrocarbon oils and halo-substituted hydrocarbon oils, such as polymerized and interpolymerized olefins (e.g., polybutylenes, polypropylenes, propylene-isobutylene copolymers, chlorinated polybutylenes, poly(1-hexenes), poly (1-octenes), poly(1-decenes)); alkylbenzenes (e.g., dodecylbenzenes, tetradecylbenzenes, dinonylbenzenes, di(2ethylhexyl)benzenes); polyphenyls (e.g. biphenyls, terphenyls, alkylated polyphenols); alkylated diphenyl ethers and alkylated diphenyl sulfides and the derivatives, analogs, and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ oxo acid diesters of tetraethylene glycol.

Another suitable class of synthetic lubricating oils comprises the esters of dicarboxylic acids (e.g., phthalic acid, succinic acids, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di-(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids, and polyols and polyol ethers such as neopentyl glycol, trimethylolpropane, pentaerythritol, dipentaerythritol, and tripentaerythritol.

Silicon-based oils such as the polyalkyl-, polyaryl-, polyalkoxy-, and polyaryloxysiloxane oils and silicate oils comprise another useful class of synthetic lubricants; they include tetraethyl silicate, tetraisopropyl silicate, tetra-(2-ethyhexyl)silicate, tetra-4-methyl-2-ethylhexyl) silicate, tetra-(p-tert-butyphenyl) silicate, hexa-(4-methyl-2-pentoxy) disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined, and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration, and percolation are known to those skilled in the art. Rerefined oils are obtained by processes similar to those used to obtain refined oils, but applied to oils that have been already in service. Such rerefined oils are also known as reclaimed or reprocessed oils and often are additionally processed by techniques for removal of spent additives and oil breakdown products.

The invention is particularly directed to engine oil formulations and additives therefor. As used herein the term "engine oil" means a lubricating oil that may be useful in an engine oil, and by way of example, includes an automotive oil or diesel engine oil. The lubricating oil compositions of the present invention are also suitable for lubrication of marine diesel engines including 4 stroke trunk piston engines and 2 stroke cross head engines.

The formulated oil should have a viscosity in the lubricating viscosity range, typically about 45 SUS at 100° F., to about 6000 SUS at 100° F. The lubricating oil also contains one or more overbased alkaline earth metal detergents, at least one of which is a metal-containing neutral and overbased salicylate based on styrenated salicylic acid as described herein. The detergent components collectively comprise an effective amount, which usually lies in a range of 0.01 wt. % up to as much as 25 wt. %, preferably 0.1–10 wt. %, more preferably 0.1 to 5.0%. Unless indicated otherwise herein, all weight percentages are by weight of the entire lubricating oil composition.

The advantages and the important features of the present invention will be more apparent from the following examples.

EXAMPLES

Comparative Example A

Overbasing 2:1 Molar Ratio Styrene: Salicylic Acid

One hundred parts of 2:1 molar styrenated salicylic acid is mixed with 200 parts of VMP naphtha and 68 parts of 100 viscosity paraffinic oil. To this are added 10 parts of neutral calcium sulfonate, 12 parts of methanol, and 30 parts of lime. The mixture is heated to 130–150° F. (54–66° C.) and carbonated with carbon dioxide at a rate of 150 mL/minute for 20 minutes.

Heat is lost during carbonation and the reaction mixture separates into two phases—one of which is insoluble in VMP naphtha.

Comparative Example B

Comparative Example A was repeated, but the aromatic solvent xylene was substituted for the VMP naphtha, and 200 viscosity naphthenic oil substituted for the paraffinic oil.

In this case, the carbonation step resulted in an exothermic reaction. The reaction product was filtered to remove unreacted solids, and heated to 380° F. (193° C.), to remove methanol and xylene.

The final product was fluid at 380° F., but when cooled to under 200° F. (93° C.), it solidified.

Comparative Example C

Overbasing 4:1 Molar Ratio Styrene: Salicylic Acid

One hundred parts of 4:1 molar styrenated salicylic acid is mixed with 200 parts of VMP naphtha and 68 parts of 200 viscosity naphthenic oil. To this mixture is added 10 parts of neutral calcium sulfonate, 12 parts of methanol, and 30 parts of lime. The mixture is heated to 130–150° F. and carbonated with carbon dioxide at a rate of 150 mL/minute for 20 minutes.

The carbonation step resulted in an exothermic reaction. However, the final product collapsed into two phases while being filtered.

Comparative Example D

One hundred parts of 4:1 molar styrenated salicylic acid is mixed with 200 parts of VMP naphtha and 60 parts of 200 viscosity naphthenic oil. To this mixture is added 60 parts of neutral calcium sulfonate, 12 parts of methanol, and 30 parts of lime. The mixture is heated to 130–150° F. and carbonated with carbon dioxide at a rate of 150 mL/minute for 20 minutes. The product is then filtered to remove excess solids and heated to 380° F. to remove methanol and VMP naphtha.

The carbonation resulted in an exothermic reaction. The final product was fluid, with a viscosity of 39 cst, and a TBN of 121; however, it exhibited poor solubility at 10% in 500 viscosity paraffinic oil.

Example 1

Calcium and Magnesium Salicylates Using Styrenated Salicylic Acid

This example describes a method to make alkyl styrene salicylic acid.

Thirty four grams (0.25 mole) of salicylic acid is added to a reactor, followed by 5 grams of p-toluenesulfonic acid, and heated to 120° C. to form a partial melt. A quantity of 312 grams (3 moles) of styrene is added dropwise over two hours, keeping the temperature between 145–160° C. After the complete addition of the styrene, the clear brown solution is maintained at 155° C. for one hour.

Example 2

Overbasing 8:1 Molar Styrene: Salicylic Acid

Sixty parts of 8:1 molar styrenated salicylic acid is mixed with 200 parts of VMP naphtha and 100 parts of 200 viscosity naphthenic oil. To this mixture is added 36 parts of neutral calcium sulfonate, 12 parts of methanol, and 40 parts of lime. The mixture is heated to 130–150° F. and carbonated with carbon dioxide at a rate of 200 mL/minute for 25 minutes. The product was then filtered to remove excess solids, and heated to 380° F. to remove methanol and VMP naphtha.

The carbonation resulted in an exothermic reaction. The final product was fluid, with a viscosity of 12 cst., and a TBN of 154.

Visual inspection of a 10 % solution of this material in 500 viscosity oil showed improved clarity over the product of Comparative Example D, but the resulting solution was still not bright and clear.

Example 3

Sixty-eight parts of 8:1 molar styrenated salicylic acid is mixed with 200 parts of VMP naphtha and 70 parts of 200 viscosity naphthenic oil. To this mixture is added 76 parts of neutral calcium sulfonate, 12 parts of methanol, and 43 parts of lime. The mixture is heated to 130–150° F. and carbonated with carbon dioxide at a rate of 200 mL/minute for 30 minutes. The product is then filtered to remove excess solids and heated to 380° F. to remove methanol and VMP naphtha.

The carbonation resulted in an exothermic reaction. The final product was fluid, with a TBN of 181.

Solubility at 10% in 500 viscosity oil was excellent, giving a product that was bright and clear.

Example 4

The alkyl salicylic acid of Example 1 is used to prepare an overbased calcium salicylate as shown below.

One hundred grams of styrene salicylic acid from Example 1 is added to a mixing vessel followed by 150 grams of naphtha and 100 grams of 600 SUS base oil. The mixture is agitated slowly and 20 grams of a neutral calcium sulfonate is charged, followed by 14 grams of methanol and 35 grams of hydrated lime.

The temperature is adjusted to 60° C. and carbon dioxide is introduced at 200 mL/minute for 30 minutes. Upon completion of the carbonation, the dark brown liquid is filtered and distilled to 220° C. to produce a clear brown solution of the desired calcium carbonate overbased calcium salicylate. The total alkalinity of the final product is about 190.

Example 5

The styrene salicylic acid of Example 1 is reacted with an overbased calcium sulfonate as shown below to produce a clear brown solution with total alkalinity of 300.

Fifty grams each of styrene salicylic acid and 500 TBN calcium sulfonate is mixed and heated to 40° C., whereupon 75 grams of naphtha and 15 grams of methanol are added. The mixture is mixed at 60° C. for one hour then heated to 220° C. to remove the volatiles. The product, when tested in the high temperature detergency panel coker test, resulted in 10.7 milligrams of deposit.

In view of the many changes and modifications that can be made without departing from principles underlying the invention, reference should be made to the appended claims for an understanding of the scope of the protection to be afforded the invention.

What is claimed is:

1. An engine oil comprising
   a) a lubricating oil, and
   b) an overbased alkaline earth metal salicylate detergent of the structure:

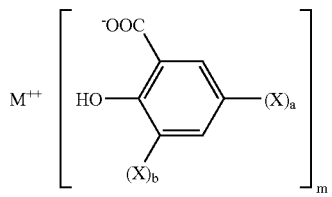

wherein:
X is

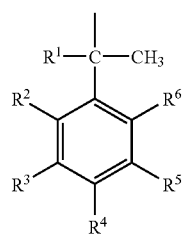

$R^1$ is selected from the group consisting of hydrogen, substituted or unsubstituted alkyl, and substituted or unsubstituted aryl;
$R^2$, $R^3$, $R^4$, $R^5$, and $R^6$ are independently selected from the group consisting of hydrogen, X, and functional groups which do not adversely affect the detergency or antioxidant properties of the overbased alkaline earth metal salicylate detergent;
a and b are independently selected integers $\geq 0$ and $a+b \geq 8$;
m is 2; and
M is an alkaline earth metal.

2. The engine oil of claim 1 wherein M is selected from the group consisting of calcium and magnesium.

3. The engine oil of claim 1 wherein $R^1$ is hydrogen or methyl.

4. The engine oil of claim 1 wherein $R^1$ is substituted or unsubstituted aryl.

5. The engine oil of claim 4 wherein $R^1$ is substituted or unsubstituted phenyl.

6. The engine oil of claim 1 wherein X is of the formula

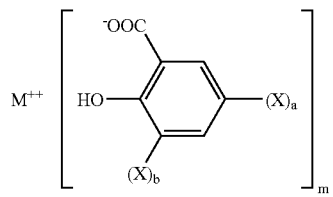

and is a moiety of a compound selected from the group consisting of styrene; 2-, 3-, or 4-methylstyrene; 2- or 4-ethylstyrene; 3- or 4-isopropylstyrene; 4-n-butylstyrene; 4-t-butylstyrene, 4-cyclohexylstyrene; 4-octylstyrene; 2,4-dimethylstyrene; 2,5-dimethylstyrene; 3- or 4-methoxystyrene, 4-ethoxystyrene; α-methylstyrene; α-ethylstyrene; α-n-butylstyrene; α-isobutylstyrene; 4-phenylstyrene; and 4-fluorostyrene,
wherein $R^1$, $R^2$, $R^3$, $R^4$, $R^5$, and $R^6$, are as defined in claim 1.

7. The engine oil of claim 6 wherein X is a moiety of styrene.

8. The engine oil of claim 1 wherein the base number is in the range of from about 60 to about 350 mg KOH/gram.

9. The engine oil of claim 1 wherein a+b is 8 to 40.

10. An engine oil comprising
    a) a lubricating oil, and
    b) an overbased alkaline earth metal salicylate detergent of the structure:

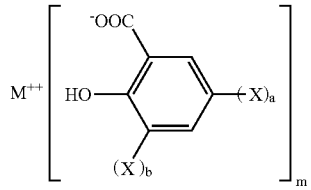

wherein:
X is of the formula

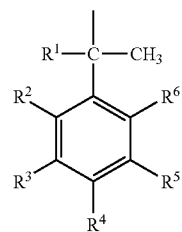

and is a moiety of a compound selected from the group consisting of styrene; 2-, 3-, or 4-methylstyrene; 2- or 4-ethylstyrene; 3- or 4-isopropylstyrene; 4-n-butylstyrene; 4-t-butylstyrene, 4-cyclohexylstyrene; 4-octylstyrene; 2,4-dimethylstyrene; 2,5-dimethylstyrene; 3- or 4-methoxystyrene, 4-ethoxystyrene; α-methylstyrene; α-ethylstyrene; α-n-butylstyrene; α-isobutylstyrene; 4-phenylstyrene; and 4-fluorostyrene;

$R^1$ is selected from the group consisting of hydrogen, substituted or unsubstituted alkyl, and substituted or unsubstituted aryl;

$R^2$, $R^3$, $R^4$, $R^5$, and $R^6$ are independently selected from the group consisting of hydrogen, X, and functional groups which do not adversely affect the detergency or antioxidant properties of the overbased alkaline earth metal salicylate detergent;

a and b are independently selected integers $\geqq 0$ and a+b is 8 to 40;

m is 2; and

M is calcium or magnesium.

* * * * *

UNITED STATES PATENT AND TRADEMARK OFFICE
CERTIFICATE OF CORRECTION

PATENT NO. : 7,087,557 B2
APPLICATION NO. : 10/626747
DATED : August 8, 2006
INVENTOR(S) : Ronald J. Muir and William D. Olson It is certified that error appears in the above-identified patent and that said Letters Patent is hereby corrected as shown below:

Col. 14 lines 9-17, the chemical formula should appear as follows:

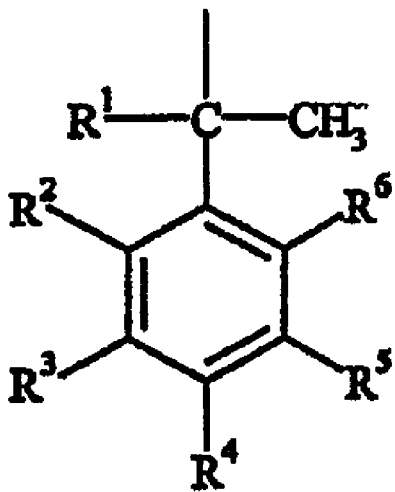

Signed and Sealed this

Twenty Second Day of April, 2008

JON W. DUDAS
*Director of the United States Patent and Trademark Office*